United States Patent
Yan

(10) Patent No.: US 11,604,949 B2
(45) Date of Patent: Mar. 14, 2023

(54) IMAGE PROCESSING METHOD AND APPARATUS, COMPUTER-READABLE STORAGE MEDIUM, AND COMPUTER DEVICE

(71) Applicant: TENCENT TECHNOLOGY (SHENZHEN) COMPANY LIMITED, Guangdong (CN)

(72) Inventor: Ke Zhou Yan, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 320 days.

(21) Appl. No.: 17/034,486

(22) Filed: Sep. 28, 2020

(65) Prior Publication Data
US 2021/0019551 A1    Jan. 21, 2021

Related U.S. Application Data

(63) Continuation of application No. PCT/CN2019/099859, filed on Aug. 8, 2019.

(30) Foreign Application Priority Data

Aug. 23, 2018    (CN) .................. 201810967559.X

(51) Int. Cl.
*G06K 9/62*    (2022.01)
*G16H 30/40*    (2018.01)
(Continued)

(52) U.S. Cl.
CPC .......... *G06K 9/627* (2013.01); *G06K 9/6256* (2013.01); *G06N 3/0454* (2013.01); *G06N 3/08* (2013.01);
(Continued)

(58) Field of Classification Search
CPC .... G06K 9/627; G06K 9/6256; G06K 9/6267; G06K 9/629; G06N 3/0454; G06N 3/08;
(Continued)

(56) References Cited

U.S. PATENT DOCUMENTS

2010/0128950 A1*    5/2010    Woods ............... A61B 6/03
                                                        382/131
2018/0053300 A1    2/2018    Podilchuk et al.
(Continued)

FOREIGN PATENT DOCUMENTS

CN    106203488 A  *  12/2016    ............. G06K 9/629
CN    106203488 A      12/2016
(Continued)

OTHER PUBLICATIONS

Written Opinion of the International Searching Authority dated Sep. 30, 2019 in International Application No. PCT/CN2019/099859.
(Continued)

*Primary Examiner* — Juan A Torres
(74) *Attorney, Agent, or Firm* — Sughrue Mion, PLLC

(57) ABSTRACT

An image processing method is provided. The method includes obtaining at least two images, the at least two images being based on the same target object captured from different imaging angles, respectively; extracting, by using feature extraction networks included in an image processing model, target features of the at least two images, the feature extraction networks being configured to extract features of images corresponding to the different imaging angles, respectively; and determining, based on the target features, a classification result corresponding to the target object.

18 Claims, 8 Drawing Sheets

(51) Int. Cl.
*G06N 3/04* (2023.01)
*G06N 3/08* (2023.01)
*G06V 10/40* (2022.01)

(52) U.S. Cl.
CPC ............ *G06V 10/40* (2022.01); *G16H 30/40* (2018.01); *G06V 2201/03* (2022.01)

(58) Field of Classification Search
CPC .... G06V 10/40; G06V 2201/03; G06V 10/82; G16H 30/40
USPC ......................................................... 382/128
See application file for complete search history.

(56) References Cited

U.S. PATENT DOCUMENTS

| | | | | |
|---|---|---|---|---|
| 2019/0005684 | A1* | 1/2019 | De Fauw | G06K 9/6271 |
| 2019/0065897 | A1* | 2/2019 | Li | G06K 9/6269 |

FOREIGN PATENT DOCUMENTS

| | | | | | |
|---|---|---|---|---|---|
| CN | 106682435 | A | * | 5/2017 | G06K 9/3233 |
| CN | 106682435 | A | | 5/2017 | |
| CN | 107169527 | A | * | 9/2017 | G06K 9/6256 |
| CN | 107169527 | A | | 9/2017 | |
| CN | 107437245 | A | | 12/2017 | |
| CN | 107492099 | A | * | 12/2017 | G06K 9/46 |
| CN | 107492099 | A | | 12/2017 | |
| CN | 107665352 | A | | 2/2018 | |
| CN | 107748900 | A | | 3/2018 | |
| CN | 107977971 | A | | 5/2018 | |
| CN | 108182441 | A | | 6/2018 | |
| CN | 108229291 | A | | 6/2018 | |
| CN | 108229291 | A | * | 6/2018 | G06K 9/00228 |
| CN | 108288035 | A | | 7/2018 | |
| CN | 108304873 | A | | 7/2018 | |
| CN | 110008971 | A | | 7/2019 | |

OTHER PUBLICATIONS

Yahong Luo, "Diagnostic mammogram", Liaoning Science and Technology Publishing, Feb. 2, 2016, 2 pages.
Dehong Cao, "Modern medical imaging technology", Shanghai Science and Technology Publishing, Sep. 2016, 3 pages.
Office Action for corresponding CN 201810967559.X, dated Aug. 27, 2020.
International Search Report for PCT/CN2019/099859, dated Sep. 30, 2019.

* cited by examiner

IMAGE PROCESSING METHOD AND APPARATUS, COMPUTER-READABLE STORAGE MEDIUM, AND COMPUTER DEVICE

CROSS-REFERENCE TO RELATED APPLICATION(S)

This application is a bypass continuation application of International Application No. PCT/CN2019/099859, filed Aug. 8, 2019, which claims priority to Chinese Patent Application No. 201810967559.X, entitled "IMAGE PROCESSING METHOD AND APPARATUS, COMPUTER-READABLE STORAGE MEDIUM, AND COMPUTER DEVICE" and filed on Aug. 23, 2018, the disclosures of which are herein incorporated by reference in their entireties.

FIELD

The disclosure relates to the field of computer technologies, and in particular, to an image processing method and apparatus, a computer-readable storage medium, and a computer device.

BACKGROUND

An image including a target object may be processed to determine whether there exists a state and/or an attribute of an associated event of the target object. For example, whether a breast has mammary cancer may be determined by processing a mammary molybdenum target image.

In the related art, an image including a target object is mainly observed manually, and then a classification result corresponding to the target object is determined based on human experience. The classification result may be used for reflecting a state and/or an attribute of an associated event of the target object. For example, a doctor observes a mammary molybdenum target image with naked eyes, and determines a classification result corresponding to a breast with medical experience. The classification result may be used for representing whether the breast has mammary cancer. However, observation and determination that are manually performed have strong subjectivity and result in relatively low efficiency and accuracy in detecting an associated event of the target object (e.g., mammary cancer).

SUMMARY

Embodiments of the disclosure provide an image processing method and an image processing apparatus, a computer-readable storage medium, and a computer device, to solve the problem of relatively low efficiency and accuracy in detecting an associated event of the target object in the related art.

According to an aspect of an example embodiment, provided is an image processing method, applied to a computer device, the method including: obtaining at least two images, the at least two images being based on the same target object captured from different imaging angles, respectively; extracting, by using feature extraction networks included in an image processing model, target features of the at least two images, the feature extraction networks being configured to extract features of images corresponding to the different imaging angles, respectively; and determining, based on the target features, a classification result corresponding to the target object.

According to an aspect of an example embodiment, provided is a model training method, applied to a computer device, the method including: obtaining at least two global image sample groups, the at least two global image sample groups being based on a sample object captured from different imaging angles, respectively; performing model training of a first neural network based on the at least two global image sample groups, and determining intermediate feature extraction networks corresponding to the at least two global image sample groups; constructing a second neural network according to the intermediate feature extraction networks; and performing model training of the second neural network based on the at least two global image sample groups, and determining an image processing model.

According to an aspect of an example embodiment, provided is an image processing apparatus, disposed in a computer device, the apparatus including: at least one memory configured to store program code; and at least one processor configured to read the program code and operate as instructed by the program code, the program code including: image obtaining code configured to cause at least one of the at least one processor to obtain at least two images, the at least two images being based on the same target object captured from different imaging angles, respectively; target feature obtaining code configured to cause at least one of the at least one processor to extract, by using feature extraction networks in an image processing model, target features of the at least two images, the feature extraction networks being configured to extract features of images corresponding to the different imaging angles, respectively; and classification result determining code configured to cause at least one of the at least one processor to determine, based on the target features, a classification result corresponding to the target object.

According to an aspect of an example embodiment, provided is a model training apparatus, disposed in a computer device, the apparatus including: at least one memory configured to store program code; and at least one processor configured to read the program code and operate as instructed by the program code, the program code including: global sample obtaining code configured to cause at least one of the at least one processor to obtain at least two global image sample groups, the at least two global image sample groups being based on a sample object captured from different imaging angles, respectively; intermediate network training code configured to cause at least one of the at least one processor to perform model training of a first neural network based on the at least two global image sample groups, and determine intermediate feature extraction networks corresponding to the at least two global image sample groups; neural network construction code configured to cause at least one of the at least one processor to construct a second neural network according to the intermediate feature extraction networks; and image processing model training code configured to cause at least one of the at least one processor to perform model training of the second neural network based on the at least two global image sample groups, and determine an image processing model.

According to an aspect of an example embodiment, provided is a non-transitory computer-readable storage medium, storing a computer program, the computer program, when executed by a processor, causing the processor to perform operations of the foregoing image processing method and/or the model training method.

According to an aspect of an example embodiment, provided is a computer device, including a memory and a processor, the memory storing a computer program, when executed by the processor, causing the processor to perform operations of the foregoing image processing method and/or the model training method.

BRIEF DESCRIPTION OF THE DRAWINGS

To describe the technical solutions in embodiments of the disclosure more clearly, the following briefly describes the accompanying drawings required for describing the embodiments of the disclosure. Apparently, the accompanying drawings in the following description show merely some embodiments of the disclosure, and a person of ordinary skill in the art may derive other drawings from the accompanying drawings without creative efforts.

DETAILED DESCRIPTION

To make objectives, technical solutions, and advantages of the embodiments of the disclosure clearer and more understandable, the embodiments of the disclosure are further described in detail below with reference to the accompanying drawings and the embodiments. The specific embodiments described herein are merely used for explaining the disclosure, but are not intended to limit the embodiments of the disclosure.

Terms such as "first" and "second" used in the embodiments of the disclosure are used for distinguishing one element from another element. However, the objects are not limited by the terms. The terms may be exchanged without departing from the scope of the embodiments of the disclosure. For example, the term "first neural network" may be described as the term "second neural network", and similarly, the term "second neural network" may be described as the term "first neural network".

In addition, the terms "include", "comprises", "have" and any variant thereof used in the embodiments of the disclosure are intended to cover non-exclusive inclusion. For example, a process, method, system, product, or device that includes a list of operations or units is not necessarily limited to those expressly listed operations or units, but may include other operations or units not expressly listed or inherent to such a process, method, system, product, or device. The term "and/or" used in the embodiments of the disclosure includes any or all combinations of one or more related listed items.

Expressions such as "at least one of," when preceding a list of elements, modify the entire list of elements and do not modify the individual elements of the list.

Figure 1:
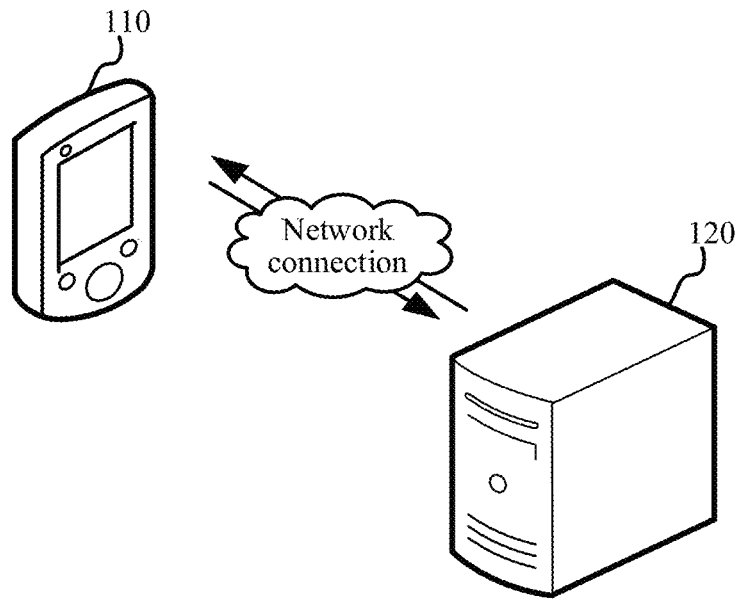
FIG. 1 is a diagram of an application environment of an image processing method and/or a model training method according to an embodiment of the disclosure.

An image processing method provided in the embodiments of the disclosure may be applied to an application environment shown in FIG. 1. The application environment may involve a terminal 110 and a server 120. The terminal 110 and the server 120 may be connected through a wired network or a wireless network.

Specifically, in the embodiments of the disclosure, a model training task may be completed on the server 120, to obtain an image processing model. After obtaining at least two images to be processed (e.g., images formed by separately capturing the same target object from different imaging angles), the terminal 110 may transmit the at least two images to the server 120. Further, the server 120 may separately extract, by using feature extraction networks corresponding to the at least two images in an image processing model, target features of the at least two images, and then, further determine, according to the target features, a classification result corresponding to the target object (or referred to as an image detection task).

Then, the model training task may alternatively be completed on the terminal 110, to obtain an image processing model. For example, the terminal 110 may complete the model training task and the image detection task independently without the involvement of the server 120.

In addition, in the embodiments of the disclosure, the image processing model may alternatively be deployed on the terminal 110. In this case, after obtaining the at least two images to be processed, the terminal 110 may directly complete the image detection task by using the image processing model stored locally without transmitting the images to the server 120.

The terminal 110 may be a smartphone, a tablet computer, a notebook computer, a desktop computer, a personal digital assistant, a wearable device, a medical imaging device, or the like, but is not limited thereto. The server 120 may be implemented by using an independent physical server or a server cluster formed by a plurality of physical servers.

Figure 2:
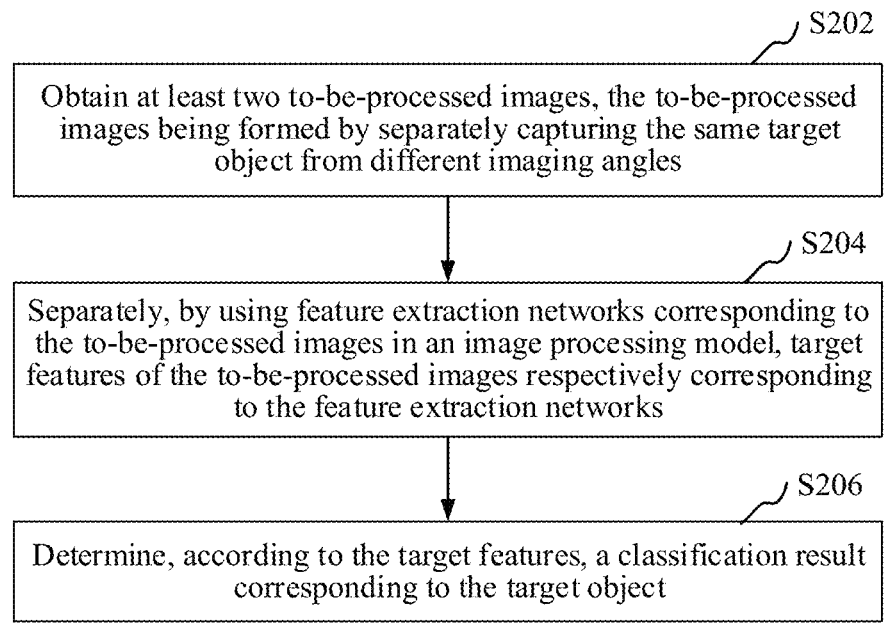
FIG. 2 is a schematic flowchart of an image processing method according to an embodiment of the disclosure.

In an embodiment of the disclosure, as shown in FIG. 2, an image processing method is provided. An example in which the method is applied to a computer device (such as the terminal 110 or the server 120 shown in FIG. 1) is described for purpose of illustration. The method may include the following operations S202 to S206.

S202. Obtain at least two images to be processed.

Each of the at least two images may be an image for which a classification result corresponding to a target object included in the image needs to be determined. In an embodiment of the disclosure, at least two images need to be obtained each time a classification result is determined. That is, the classification result is determined according to the at least two images, and the images are formed by separately capturing the same target object from different imaging angles. The images correspond to the imaging angles. For example, the classification result is determined based on the two images (hereinafter, referred to as a first image and a second image). The first image is formed by capturing the target object from a first imaging angle, and the second image is formed by capturing the target object from a second imaging angle different from the first imaging angle. The first image corresponds to the first imaging angle, and the second image corresponds to the second imaging angle. A specific quantity of images to be processed is not limited to two, but may be determined as appropriate according to an embodiment and may be equal to or greater than two. This is not specifically limited in an embodiment of the disclosure. For example, the classification result may alternatively be determined according to three images to be processed, and the three images are formed by separately capturing the same target object from different imaging angles.

The imaging angle may change along with a position of an imaging device and a position of an imaged object. More than one captured image may be formed by capturing the same object from different imaging angles, and the captured images separately include the target object form different imaging angles. That is, the target object is presented from different presentation angles. In addition, in the field of medical imaging, the imaging angle may refer to a projection position. For example, projection positions that are used in forming a mammary molybdenum target image may include a craniocaudal position (CC position), a mediolateral oblique position (MLO position), a lateromedial position (LM position), a lateromedial oblique position (LMO position), an axillary tail position (AT position), and the like.

Subsequently, when the classification result corresponding to the target object needs to be determined, the images may be obtained according to the captured images, and the obtained images separately include the target object from different imaging angles. In an embodiment, at least two captured images formed by capturing the same target object from different imaging angles may be obtained, and the obtained captured images are the images to be processed. In another embodiment, after the at least two captured images formed by capturing the same target object from different imaging angles are obtained, the captured images may be separately preprocessed, to obtain the images to be processed corresponding to the captured images.

In the imaging process, the captured images may be affected by external environment factors or noise generated during running of the imaging device. Consequently, the generated captured images may include noise. If the captured images including the noise are directly used as the images to be processed based on which the classification result is determined, the accuracy of classification is reduced. Accordingly, preprocessing of the captured image may include de-noising processing of the captured image. In addition, an original image size of the captured image may not meet a predetermined size condition, and accordingly, the preprocessing of the captured image may include image size adjustment processing of the captured images, to adjust the captured image to meet the predetermined size condition, and to obtain the image to be processed. The preprocessing may alternatively include both the de-noising processing and the image size adjustment processing.

In an embodiment, the image may be a medical image, and accordingly, the target object may be an organism or a body portion of an organism. The medical image is an internal tissue image obtained from an organism or a body portion of an organism in a non-invasive manner for medical treatment or medical research. According to an image imaging manner, the medical images may include an ultrasonic image obtained by scanning with an ultrasonic beam and by receiving and processing a reflected signal, a computed tomography (CT) image obtained through CT, or a magnetic resonance (MR) image obtained through MR imaging.

When the images are medical images, the medical images are distinguished according to the target object included in the images, and the images to be processed may be mammary molybdenum target images including a breast as the target object. In this case, the classification result corresponding to the target object may be used for reflecting a state and/or an attribute of mammary cancer. In an embodiment, imaging angles of mammary molybdenum target images may include the CC position and the MLO position, and accordingly, obtained at least two images may include: a mammary molybdenum target image formed by capturing (e.g., photographing) the breast in the CC position and a mammary molybdenum target image formed by capturing (e.g., photographing) the breast in the MLO position. However, these are merely examples and the disclosure is not limited thereto.

During an example application of the disclosure, the image to be processed may alternatively be a sinus image of including a sinus as a target object. In this case, the classification result corresponding to the target object may be used for reflecting a state and/or attribute of paranasal sinusitis. In an embodiment, an imaging angle of the sinus image may include a Caldwell position and a Water position, and accordingly, at least two images to be processed may include: a sinus image obtained by photographing a sinus in the Caldwell position and a sinus image obtained by photographing the sinus in the Water position.

In another embodiment, the images may alternatively include images of various other types such as a character image, an animal image, a plant image, and an architectural image.

S204. Separately extract, by using feature extraction networks corresponding to the images to be processed in an image processing model, target features of the images respectively corresponding to the feature extraction networks.

The image processing model is a machine learning model having a capability of image recognition. The image recognition may be extracting features in the images and classifying the images according to the features. The machine learning model is obtained through model training according to sample data. The image processing model obtained through model training can learn a mapping rule between the image features and the classification results from image samples, and obtain a corresponding classification result of a new image according to the mapping rule. In an embodiment, the image processing model may include a convolutional neural network (CNN).

The feature extraction network is a component of the image processing model, and may be configured to perform feature extraction on the image, to obtain the target feature of the image. The target feature may be a feature map corresponding to the image, and a data type of the target feature may be a vector.

The image processing model includes the feature extraction networks corresponding to the obtained images, and the feature extraction networks are independent of each other, and are configured to extract the target features of the images corresponding to the imaging angles. The images may correspond to the imaging angles, the feature extraction networks may also respectively correspond to the imaging angle, and accordingly, the images may respectively correspond to the feature extraction networks. For example, an image DP1 formed by capturing the target object from an imaging angle PO1 and an image DP2 formed by capturing the target object from an imaging angle PO2 are obtained. If the image processing model includes a feature extraction network FEN1 corresponding to the imaging angle PO1 and a feature extraction network FEN2 corresponding to the imaging angle PO2, the feature extraction network FEN1 corresponds to the image DP1, and the feature extraction network FEN2 corresponds to the image DP2.

A network framework of the feature extraction network may be built by itself starting from zero existing network framework according to an embodiment, or may be obtained by reconstructing an existing network framework having the feature extraction function. For example, an existing convolutional neural network framework generally includes: a feature extraction part including a convolution layer and a pooling layer and used for performing feature extraction, and a classification output part including a fully connected layer and a Softmax layer. When the existing convolutional neural network framework is reconstructed, the classification output part of the existing convolutional neural network framework may be removed, and the remaining feature extraction part after removal may be used as the network framework of the feature extraction network.

In an embodiment, after the images are obtained, the images are inputted to the image processing model. Within the image processing model, feature extraction may be performed through the feature extraction networks independent of each other on the images respectively corresponding to the feature extraction networks, to obtain target features corresponding to the images.

S206. Determine, according to the target features, a classification result corresponding to the target object.

The classification result may be used for reflecting a state/attribute of an associated event of the target object. In an embodiment, the classification result may include a probability that the target object belongs to a predetermined classification category. Content of the predetermined classification category is related to the state/attribute of the associated event, and a quantity of predetermined classification categories and content thereof may all be preset according to actual conditions.

An example in which the image is a medical image is used. Two predetermined classification categories, diseased and normal (that is, not diseased), may be included. Specifically, when the image is a mammary molybdenum target image, a classification result corresponding to the target object may include a probability that a breast has mammary cancer and a probability that the breast does not have mammary cancer. Subdivision of classification may be further performed for different disease states, and further, predetermined classification categories respectively corresponding to subdivided branches are included. In the example in which the image is the mammary molybdenum target image, the classification result corresponding to the target object may include, for example but not limited to, a probability that the breast has a benign mass, a probability that the breast has benign calcification, a probability that the breast has a malignant mass, a probability that the breast has malignant calcification, and a probability that the breast has normal gland.

In an embodiment, after the respective target features are obtained by using the image processing model, the operation of determining, according to the target features, a classification result corresponding to the target object may be continuously obtained by using the image processing model. In an embodiment, the image processing model includes a classification output network, and the operation of determining, according to the target features, a classification result corresponding to the target object may be obtained by using the classification output network. In this case, the image processing model is essentially a deep neural network model implementing end-to-end processing, that is, directly inputting the image to the model, and further, the model directly outputs the classification result without manually designing input features of the model.

For a software product using the image processing method provided in the embodiments of the disclosure, the software product may provide services in a software interface manner. A mammary molybdenum target image is used as an example. An input of the software product may separately be a mammary molybdenum target image of a breast photographed in the CC position and a mammary molybdenum target image of the breast photographed in the MLO position, and an output of the software product may be a probability that the breast has mammary cancer.

In another implementation, an image including a target object from a single imaging angle may alternatively be obtained, the single image is inputted to the machine learning model, and a classification result corresponding to the target object is outputted by using the machine learning model. Correspondingly, the machine learning model is obtained by performing model training according to image samples including a target object from a single imaging angle.

A mammary molybdenum target image is used as an example. A mammary molybdenum target image including a breast in the CC position may be obtained, the mammary molybdenum target image is inputted to the machine learning model, and a corresponding classification result is outputted by using the machine learning model. Correspondingly, the machine learning model is obtained by performing model training according to mammary molybdenum target image samples including the breast in the CC position.

However, on the one hand, in the single-imaging angle manner, an image including a complete target object is directly used for model training, and the model is expected to learn to search the whole image for features that distinguish different classification results (for example, whether mammary cancer exists or not). In this case, the model training needs a large quantity of image samples, and the training has randomness, so the model may not be capable of learning of a key feature that can most distinguish different classification results. On the other hand, a classification result obtained through an image including a target object from a single imaging angle has an undiversified classification basis, and therefore, accuracy of the classification result is low.

According to the image processing method provided in an embodiment, the at least two images formed by separately capturing the same target object from different imaging angles are obtained, target features of the images respectively corresponding to feature extraction networks are separately extracted through the feature extraction networks corresponding to the images in an image processing model, and the classification result corresponding to the target object is further determined according to the target features. On the one hand, the machine learning model automatically learns of the features in the image, and further obtains the classification result without manual participation, thereby improving efficiency of obtaining the classification result. Additionally, according to an embodiment, the classification result is determined by combining the images formed by separately capturing the same target object from different imaging angles, thereby effectively improving classification accuracy.

Figure 3:
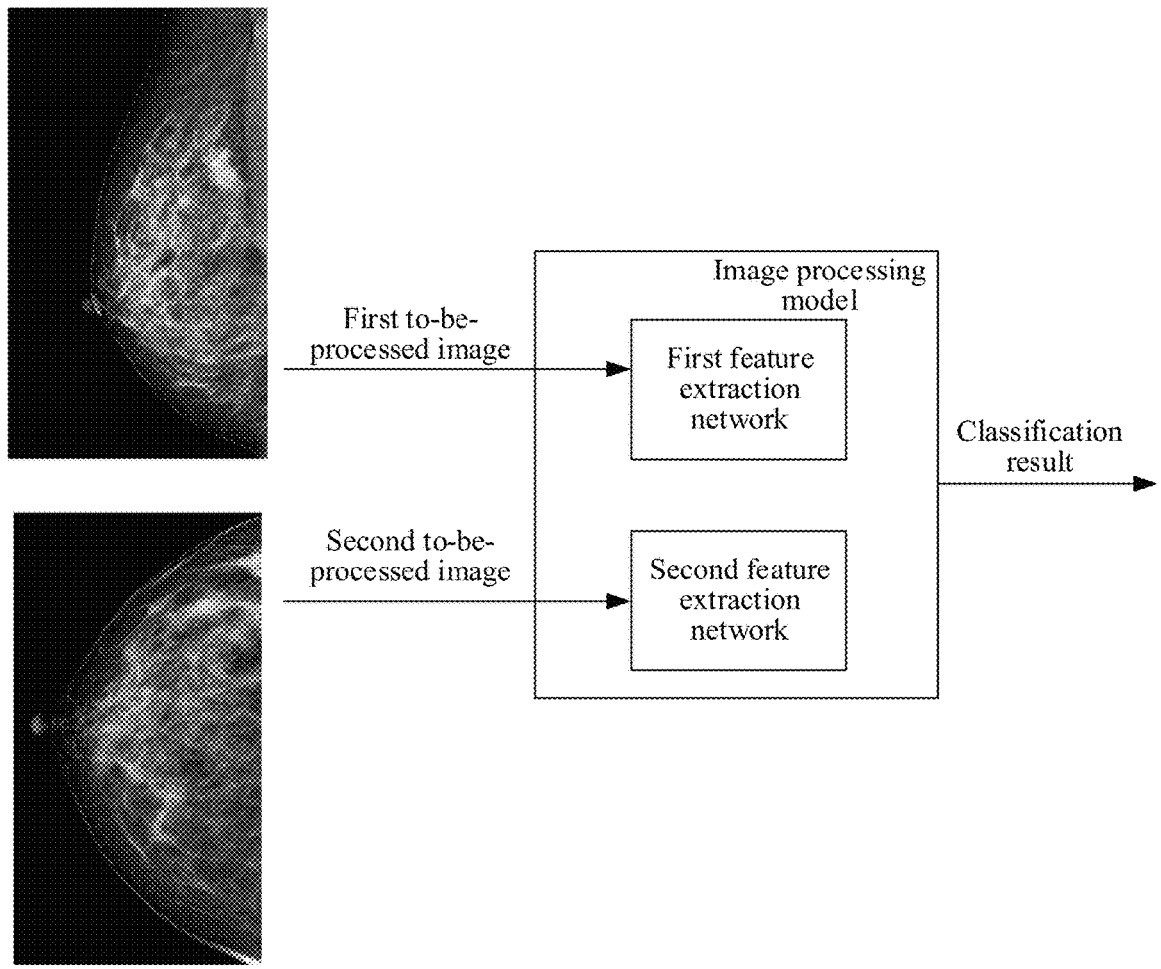
FIG. 3 is a structural block diagram of an image processing model according to an embodiment of the disclosure.

In an embodiment, as shown in FIG. 3, the at least two images include: a first image formed by capturing the target object from a first imaging angle, and a second image formed by capturing the target object from a second imaging angle different from the first imaging angle. The feature extraction networks in the image processing model include: a first feature extraction network corresponding to the first image and a second feature extraction network corresponding to the second image.

Accordingly, the operation of separately extracting, by using feature extraction networks corresponding to the images in an image processing model, target features of the images may include the following operations: extracting, by using the first feature extraction network in the image processing model, a first target feature corresponding to the first image; and extracting, by using the second feature extraction network in the image processing model, a second target feature corresponding to the second image. In addition, the operation of determining, according to the target features, a classification result corresponding to the target object may include the following operation: determining, according to the first target feature and the second target feature, the classification result corresponding to the target object.

In an embodiment of the disclosure, the classification result is determined according to the two images. An example in which the image is a mammary molybdenum target image is used. A first mammary molybdenum target image formed by photographing a breast in the CC position and a second mammary molybdenum target image formed by photographing the breast in the MLO position may be obtained. The first mammary molybdenum target image and the second mammary molybdenum target image are inputted to the image processing model. A first target feature corresponding to the first image is extracted by using a first feature extraction network corresponding to the first mammary molybdenum target image in the image processing model, and a second target feature corresponding to the second image is extracted by using the second feature extraction network corresponding to the second mammary molybdenum target image in the image processing model. The first feature extraction network and the second feature extraction network are feature extraction networks independent of each other.

In an embodiment, the operation of determining, according to the target features, a classification result corresponding to the target object, that is, operation S206, may include the following operation: performing classification according to the target features through a fully connected layer in the image processing model, to determine the classification result corresponding to the target object.

The fully connected layer may be configured to perform classification according to the features. Specifically, the fully connected layer is configured to map distributed features to a sample marking space, generally, that is, integrate the feature map into numerical values.

In an embodiment, the image processing model includes the fully connected layer. After the target features of the images are extracted by using the feature extraction networks in the image processing model, classification may be continuously performed according to the target features through the fully connected layer in the image processing model, to determine the classification result corresponding to the target object. In an embodiment, the target features outputted by the feature extraction networks may be directly inputted to the fully connected layer for classification.

Figure 4:
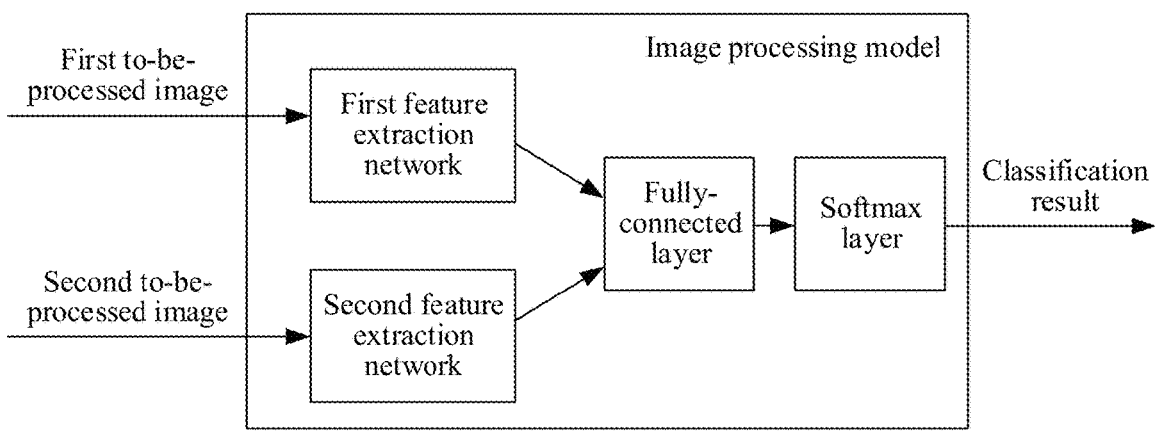
FIG. 4 is a structural block diagram of an image processing model according to an embodiment of the disclosure.

In an embodiment, after the classification is performed through the fully connected layer in the image processing model, an output result of the fully connected layer may be directly used as the classification result corresponding to the target object. In another embodiment, as shown in FIG. 4 (two feature extraction networks are used as an example in FIG. 4), the image processing model may further include a Softmax layer disposed following the fully connected layer, and the Softmax layer may be configured to map the output result of the fully connected layer to a numerical value in an interval of (0, 1) and perform normalization processing. In this case, after the classification is performed through the fully connected layer in the image processing model, the output result of the fully connected layer may alternatively be continuously mapped to the numerical values in the interval of (0, 1) through the Softmax layer in the image processing model and normalized, and then the output result of the Softmax layer is used as the classification result corresponding to the target object.

In an embodiment, the method may further include, prior to performing the operation of performing classification according to the target features through the fully connected layer in the image processing model, to determine a classification result corresponding to the target object, the following operation: sequentially performing convolution through a convolution layer in the image processing model and performing pooling through a pooling layer in the image processing model on the target features, to obtain intermediate features. Accordingly, the operation of performing classification according to the target features through the fully connected layer in the image processing model, to determine a classification result corresponding to the target object may include the following operation: performing classification according to the intermediate features through the fully connected layer in the image processing model, to determine the classification result corresponding to the target object.

Figure 5:
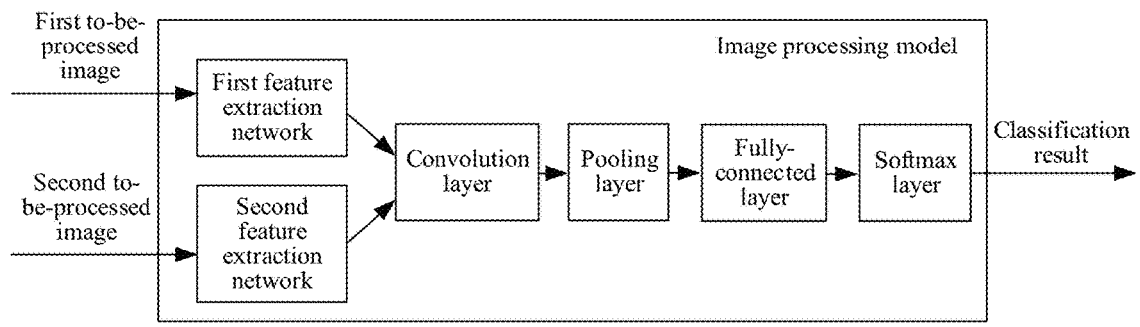
FIG. 5 is a structural block diagram of an image processing model according to an embodiment of the disclosure.

In an embodiment of the disclosure, as shown in FIG. 5, the image processing model may further include the convolution layer and the pooling layer disposed before the fully connected layer. The convolution layer may be configured to extract features through a convolution kernel. The pooling layer may be configured to reduce, through pooling, a dimension of the features outputted by the convolution layer, and the pooling generally includes two forms: mean pooling and max pooling.

In an embodiment of the disclosure, within the image processing model, after the target features of the images are extracted by using the feature extraction networks, the target features are first inputted to the convolution layer for convolution, to extract further features, then, the output result of the convolution layer is inputted to the pooling layer for pooling, to reduce the feature dimension, and further, the output result (that is, the intermediate feature) of the pooling layer is inputted to the fully connected layer for classification. According to an embodiment, a plurality of times of convolution processing and a plurality of times of pooling processing may be performed before the fully connected layer.

In an embodiment, a manner of determining the image processing model may include: obtaining at least two global image sample groups, the global image sample groups being formed by separately capturing a sample object from different imaging angles; separately performing model training of a first neural network according to the global image sample groups, and determining intermediate feature extraction networks corresponding to the global image sample groups; constructing a second neural network according to the intermediate feature extraction networks; and performing model training of the second neural network according to the global image sample groups, and determining the image processing model.

A global image sample is an image sample including a complete sample object. One global image sample group includes several global image samples formed by capturing different sample objects from the same imaging angle. A mammary molybdenum target image sample is used as an example. The one global image sample group may include three mammary molybdenum target image samples, and the three mammary molybdenum target image samples may be formed by separately photographing a complete breast BR1 in the CC position, a complete breast BR2 in the CC position, and a complete breast BR3 in the CC position.

The global image sample groups are formed by separately capturing the different sample objects from the same imaging angle. Each global image sample group uniquely corresponds to an imaging angle. For example, three global image sample groups (named as a global image sample group G1, a global image sample group G2 and a global image sample group G3 respectively) are obtained. The global image sample group G1 corresponds to an imaging angle IA1, the global image sample group G2 corresponds to an imaging angle IA2, and the global image sample group G3 corresponds to an imaging angle IA3. The imaging angles IA1, IA2, and IA3 are different from each other.

The image sample is an image whose true classification result is known. Specifically, the image sample may have a category label. The category label is used for representing the true classification result of the image sample. The mammary molybdenum target image sample is used as an example. A mammary molybdenum target image sample MGS1 has a category label used for representing that a breast in the mammary molybdenum target image sample MGS1 has mammary cancer, and a mammary molybdenum target image sample MGS2 has a category label used for representing that a breast in the mammary molybdenum target image sample MGS2 does not have mammary cancer. In an embodiment, the actual classification result represented by the category label may be determined through manual analysis, for example, is determined through analysis made by experts in the related art.

The first neural network is a neural network that needs to perform model training, and is the prototype of the intermediate feature extraction network. Specifically, the first neural network may be an initial neural network that is not pre-trained, or may be a pre-trained neural network obtained after the initial neural network is pre-trained. The first neural network may be essentially a convolutional neural network.

The model training is the process of adjusting model parameters in layers of the model. Specifically, for any global image samples group, prediction classification results of the global image samples in the global image sample group may be obtained by using the first neural network, a loss parameter (that is, a loss) is further calculated by comparing the prediction classification results of the global image samples with category labels thereof, and back propagation is then performed according to the loss parameter, to adjust the model parameters of the first neural network, to obtain an intermediate feature extraction network corresponding to the global image sample group.

The model training is an iterative processing procedure that stops training until a training stop condition is met. The training stop condition is a condition for triggering to stop model training. The training stop condition may be that a preset quantity of iterations is reached, or may be that the loss parameter obtained through calculation meets the predetermined condition. For example, the loss parameter is less than a predetermined loss threshold, or the loss parameter obtained through calculation is no longer reduced.

The intermediate feature extraction network is the prototype of the feature extraction networks in the image processing model. The intermediate feature extraction networks correspond to the feature extraction networks in the image processing model. In addition, the intermediate feature extraction networks correspond to the global image sample groups respectively. That is, model training of a first model is performed according to one global image sample group, to obtain an intermediate feature extraction network corresponding to the global image sample group.

For example, the global image samples include two mammary molybdenum target image sample groups (hereinafter, referred to as a mammary molybdenum target image sample group G-BR1 and a mammary molybdenum target image sample group G-BR2 respectively). The mammary molybdenum target image sample group G-BR1 includes several mammary molybdenum target image samples formed by photographing different complete breasts in the CC position, and the mammary molybdenum target image sample group G-BR2 includes several mammary molybdenum target image samples formed by photographing different complete breasts in the MLO position (an example E-1). In this case, model training of the first neural network is performed according to the mammary molybdenum target image samples in the mammary molybdenum target image sample group G-BR1, to obtain an intermediate feature extraction network IN1 corresponding to the mammary molybdenum target image sample group G-BR1. The intermediate feature extraction network IN1 corresponds to the CC position. In addition, the model training of the first neural network is performed according to the mammary molybdenum target image samples in the mammary molybdenum target image sample group G-BR2, to obtain an intermediate feature extraction network IN2 corresponding to the mammary molybdenum target image sample group G-BR2. The intermediate feature extraction network IN2 corresponds to the MLO position.

Figure 6:
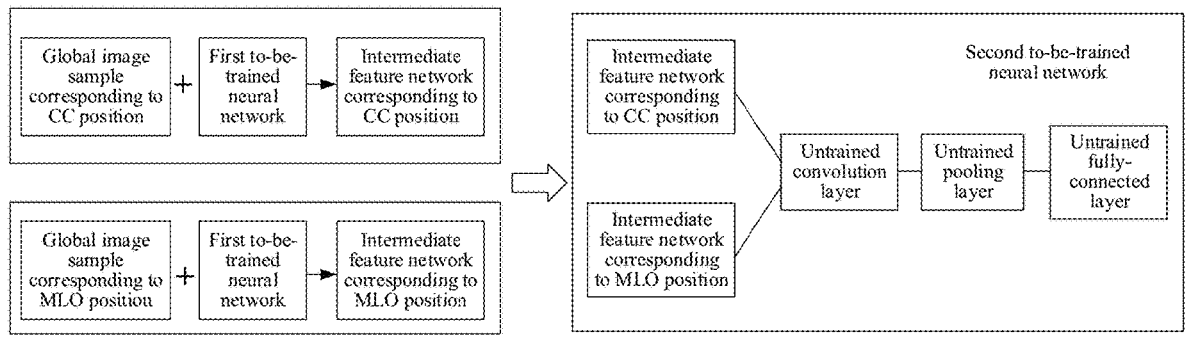
FIG. 6 is a schematic diagram of constructing a second neural network according to an embodiment of the disclosure.

After the intermediate feature extraction networks are obtained, a second neural network may be jointly constructed according to the intermediate feature extraction networks. Specifically, the classification output part (for example, the fully connected layer is removed, or when the Softmax layer is further connected following the fully connected layer, the fully connected layer and the Softmax layer may be removed together) in the intermediate feature extraction network may be separately removed, remaining intermediate feature extraction networks (or referred to as remaining networks) are in a parallel state after the removal, and an untrained convolution layer, an untrained pooling layer, and an untrained fully connected layer are sequentially connected following the remaining networks, to obtain the second neural network. In addition, for the foregoing example E-1, a schematic diagram of obtaining the second neural network may be shown in FIG. 6.

The second neural network is the prototype of the image processing model. The second neural network may simultaneously receive two or more global image sample groups as inputs.

In an embodiment, in the process of performing model training of the second neural network according to the global image sample groups, all remaining networks may be frozen first (that is, model parameters of the remaining networks keep unchanged), and model parameters of a frozen part that is not frozen (the untrained convolution layer, the untrained pooling layer, and the untrained fully connected layer) in the second neural network are adjusted according to the global image sample groups. When a first training stop condition is met, all the remaining networks is unfrozen. The model parameters of the whole second neural network are adjusted according to the global image sample groups, the training is not ended until a second training stop condition is met, and the model parameters corresponding to when the training ends are the model parameters of the image processing model.

In another embodiment, in the process of performing model training of the second neural network according to the global image sample groups, alternatively, only some of the remaining networks may be frozen. In this case, the part that is not frozen includes the remaining networks that are not frozen, the untrained convolution layer, the untrained pooling layer, and the untrained fully connected layer.

A specific training manner of performing model training of the second neural network according to the global image sample groups may be any possible model training manner, and is not limited to the foregoing training manners, that is, freezing all the remaining networks and freezing some of the remaining networks.

In an embodiment, before the operation of separately performing model training of a first neural network according to the global image sample groups, and determining intermediate feature extraction networks corresponding to the global image sample groups, the method may further include the following operations: performing parameter initialization processing on a first initial neural network, to obtain first initial parameters; and determining the first neural network according to the first initial parameters.

The initial neural network is a network framework without model parameters. The parameter initialization processing on the initial neural network may be specifically: giving randomly determined parameters or manually specified parameters to layers in the initial neural network.

In an embodiment of the disclosure, the intermediate feature extraction networks are trained on the global image sample groups starting from zero. Specifically, random initialization is performed on the model parameters of the first initial neural network, to obtain the first initial parameters, and the first initial parameters are loaded into the first initial neural network, to obtain a first neural network, and further, model training of the first neural network is performed separately according to the global image sample groups, to obtain intermediate feature extraction networks corresponding to the global image sample groups.

In an embodiment, before the operation of separately performing model training of a first neural network according to the global image sample groups, and determining intermediate feature extraction networks corresponding to the global image sample groups, the method may further include the following operations: obtaining a local image sample of a target region including a sample object; performing parameter initialization processing on a second initial neural network, to obtain a second initial parameter; and performing model training of the second initial neural network according to the local image sample and the second initial parameter, to obtain the first neural network.

The local image sample is an image sample of the target region including only the sample object. The local image sample may be regarded as a local part of the global image sample. Specifically, the target region may be cut from the global image sample, to form the local image sample. An example in which the image sample is a medical image is used. The target region may include a lesion region. The global image sample may be an image sample including a complete organism portion. The local image sample may be an image sample including the lesion region in the organism region. More specifically, an example in which the image sample is the mammary molybdenum target image is used. The global image sample may be an image sample including a complete breast. The local image sample may be an image sample including a tumor region in the breast.

Similar to the global image sample, the local image sample also has a category label. An example in which the image sample is the mammary molybdenum target image is used. The obtained local image samples may include, for example, the following five category labels: category labels used for representing that the breast has a benign mass, benign calcification, a malignant mass, malignant calcification, and normal gland.

In an embodiment of the disclosure, the model training may be first performed on the second initial neural network according to the local image sample, to obtain the first neural network. The first neural network is a pre-trained neural network instead of an initial neural network. Subsequently, migration learning is performed by using the first neural network obtained through pre-training, to obtain the intermediate feature extraction networks without training the intermediate feature extraction networks on the global image sample groups starting from zero.

Figure 7:
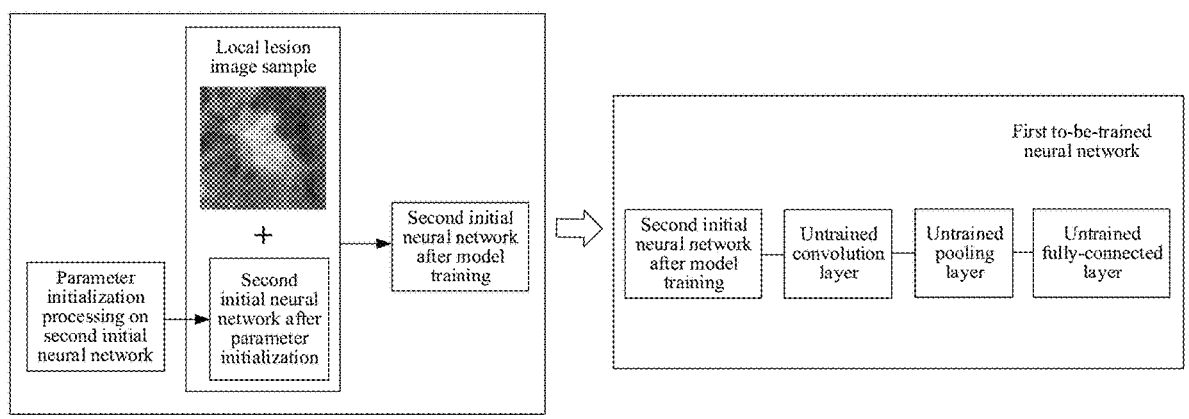
FIG. 7 is a schematic diagram of constructing a first neural network according to an embodiment of the disclosure.

Specifically, model training of the second initial neural network may be performed according to the local image sample and the second initial parameter; the trained second initial neural network (or referred to as a local processing model) is obtained when the training ends; the untrained convolution layer, the untrained pooling layer and the untrained fully connected layer may be further sequentially accessed after the local processing model, to obtain a reconstructed neural network; and random initialization processing is performed on parameters of the untrained convolution layer, the untrained pooling layer, and the untrained fully connected layer in the reconstructed neural network, to determine the first neural network. In addition, an example in which the local image sample is a local lesion image sample is used. A schematic diagram of obtaining the first neural network may be shown in FIG. 7.

Through the local-to-global training mode, the model is guided to learn features of the local region, and then, the image processing model is trained based on the features of the local region and the global image, so that image processing model can learn of key features distinguishing different classification results more effectively, and samples required for training are reduced.

When the image processing model according to an embodiment is applied to the medical image, whether a corresponding disease exists is determined according to whether the target object has a malignant lesion. A first image is first obtained through training by using a local image sample including a lesion region, the first model is guided to learn of features of a local lesion, and then, training is further performed according to the first model to obtain an image processing model configured to determine a classification result according to an image including a complete target object, so that the image processing model may more effectively learn of features for determining whether the target object has the corresponding disease.

Figure 8:
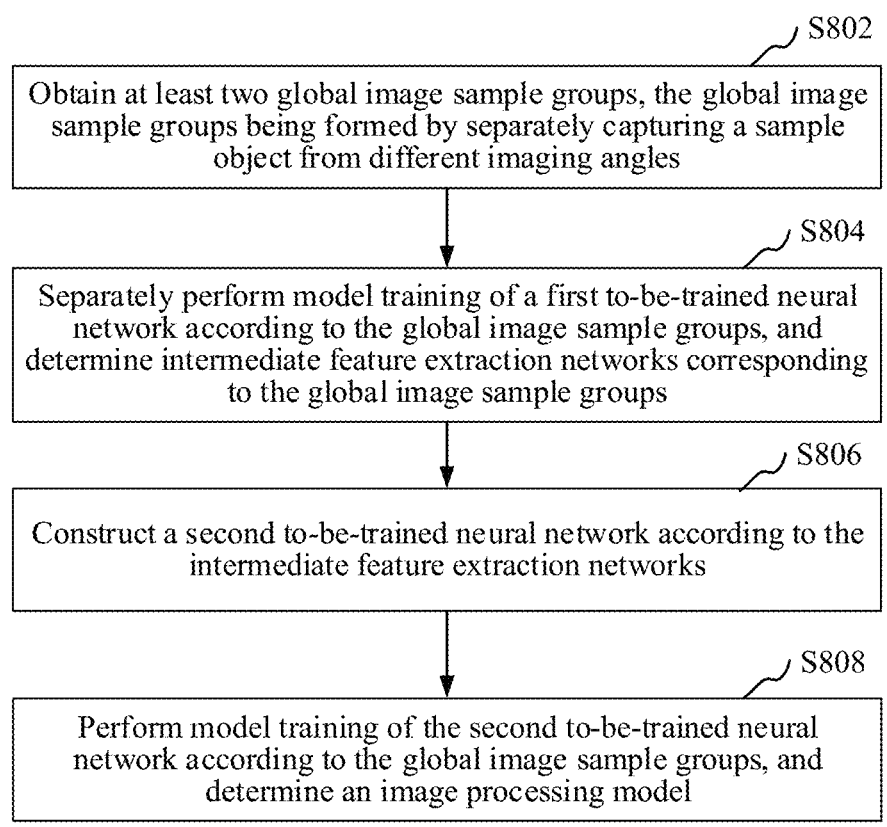
FIG. 8 is a schematic flowchart of a model training method according to an embodiment of the disclosure.

In an embodiment, as shown in FIG. 8, a model training method is provided. The method may be applied to a computer device (the terminal 110 or the server 120 shown in FIG. 1). The method may include the following operations S802 to S808.

S802. Obtain at least two global image sample groups, the global image sample groups being formed by separately capturing a sample object from different imaging angles.

S804. Separately perform model training of a first neural network according to the global image sample groups, and determine intermediate feature extraction networks corresponding to the global image sample groups.

S806. Construct a second neural network according to the intermediate feature extraction networks.

S808. Perform model training of the second neural network according to the global image sample groups, and determine an image processing model.

In an embodiment, before the operation of separately performing model training of a first neural network according to the global image sample groups, and determining intermediate feature extraction networks corresponding to the global image sample groups, that is, before operation S804, the method may further include the following operations: performing parameter initialization processing on a first initial neural network, to obtain first initial parameters; and determining the first neural network according to the first initial parameters.

In an embodiment, before the operation of separately performing model training of a first neural network according to the global image sample groups, and determining intermediate feature extraction networks corresponding to the global image sample groups, that is, before operation S804, the method may further include the following operations: obtaining a local image sample of a target region including a sample object; performing parameter initialization processing on a second initial neural network, to obtain a second initial parameter; and performing model training of the second initial neural network according to the local image sample and the second initial parameter, to obtain the first neural network.

In an embodiment, the local image sample includes a medical image sample, and the target region includes a lesion region.

The image processing model obtained using the model training method provided in the embodiments of the disclosure may be used for image classification. Specifically, the image processing model may be configured determine a classification result corresponding to a target object included in the image. For example, when applied to a medical image, the image processing model may be configured to determine a disease classification result corresponding to an organism portion in the medical image. More specifically, when applied to a mammary molybdenum target image, the image processing model may be configured to determine whether a breast has mammary cancer in the mammary molybdenum target image or a mammary cancer lesion category (e.g., a benign mass, benign calcification, a malignant mass, malignant calcification, and normal gland) corresponding to the breast.

The specific details of the technical features in an embodiment of the model training method may be same as the details of the foregoing corresponding technical features, and details are not described herein again.

Figure 9:
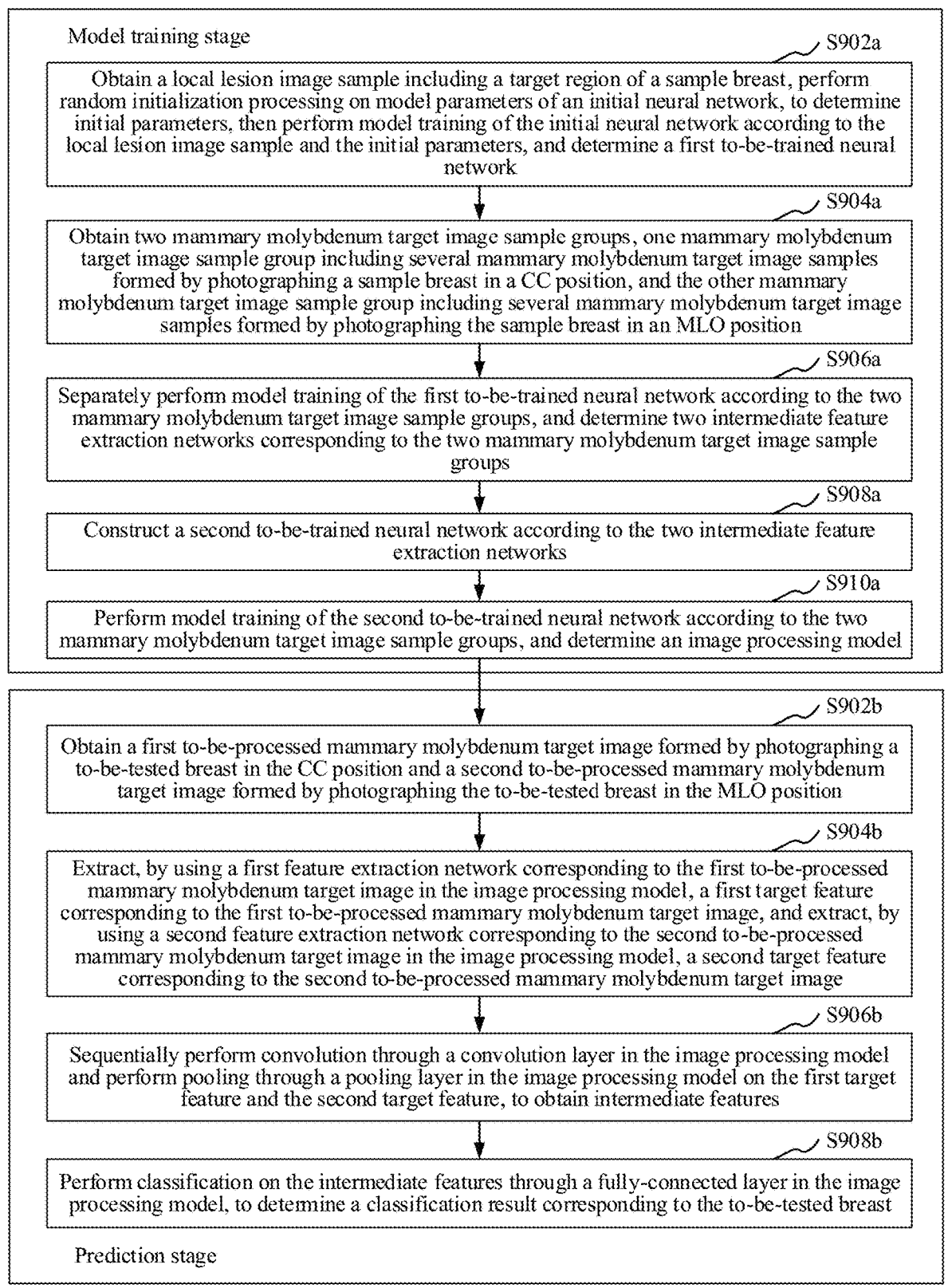
FIG. 9 is a schematic flowchart of another image processing method according to an embodiment of the disclosure.

In an embodiment, as shown in FIG. 9, an image processing method is provided. Descriptions are made by using an example in which the method is applied to a mammary molybdenum target image. The method may include the following operations: operations S902a to S910a and operations S902b to S908b.

S902a. Obtain a local lesion image sample including a target region of a sample breast, perform random initialization processing on model parameters of an initial neural network, to determine initial parameters, then perform model training of the initial neural network according to the local lesion image sample and the initial parameters, and determine a first neural network.

S904a. Obtain two mammary molybdenum target image sample groups, one mammary molybdenum target image sample group including several mammary molybdenum target image samples formed by capturing (e.g., photographing) a sample breast in a CC position, and the other mammary molybdenum target image sample group including several mammary molybdenum target image samples formed by capturing (e.g., photographing) the sample breast in an MLO position.

S906a. Separately perform model training of the first neural network according to the two mammary molybdenum target image sample groups, and determine two intermediate feature extraction networks corresponding to the two mammary molybdenum target image sample groups.

S908a. Construct a second neural network according to the two intermediate feature extraction networks.

S910a. Perform model training of the second neural network according to the two mammary molybdenum target image sample groups, and determine an image processing model.

S902b. Obtain a first mammary molybdenum target image formed by capturing (e.g., photographing) a breast in the CC position and a second mammary molybdenum target image formed by capturing (e.g., photographing) the breast in the MLO position.

S904b. Extract, by using a first feature extraction network corresponding to the first mammary molybdenum target image in the image processing model, a first target feature corresponding to the first mammary molybdenum target image, and extract, by using a second feature extraction network corresponding to the second mammary molybdenum target image in the image processing model, a second target feature corresponding to the second mammary molybdenum target image.

S906b. Sequentially perform convolution through a convolution layer in the image processing model and perform pooling through a pooling layer in the image processing model on the first target feature and the second target feature, to obtain intermediate features.

S908b. Perform classification on the intermediate features through a fully connected layer in the image processing model, to determine a classification result corresponding to the breast.

The specific details of the technical features in an embodiment of the image processing method may be same as the details of the foregoing corresponding technical features, and details are not described herein again.

While the operations in the flowcharts related to the foregoing embodiments are displayed sequentially according to the indications of the arrows, the operations are not necessarily performed sequentially according to the sequence indicated by the arrows. Unless explicitly specified in the disclosure, the operations are performed without any limitation to a sequence of operations, and may be performed in another sequence. Additionally, at least some operations may include a plurality of sub-operations or a plurality of stages, the sub-operations or stages are not necessarily performed at a same moment and may be performed at different moments, the sub-operations or stages are not necessarily sequentially performed, and the sub-operations or stages and at least some of other operations or sub-operations or stages of other operations may be performed in turn or alternately.

Figure 10:
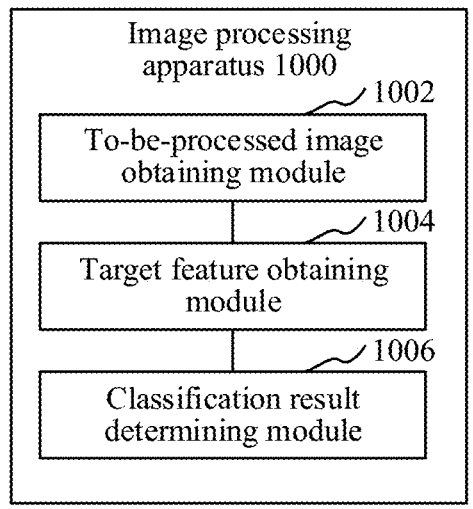
FIG. 10 is a structural block diagram of an image processing apparatus according to an embodiment of the disclosure.

In an embodiment, as shown in FIG. 10, an image processing apparatus 1000 is provided. The apparatus may be disposed in a computer device, and may include the following modules 1002 to 1006.

An image obtaining module 1002 is configured to obtain at least two images, the images being formed by separately capturing the same target object from different imaging angles.

A target feature obtaining module 1004 is configured to separately extract, by using feature extraction networks corresponding to the images in an image processing model, target features of the images respectively corresponding to the feature extraction networks, the feature extraction networks being configured to extract features of the images corresponding to the imaging angles.

A classification result determining module 1006 is configured to determine, according to the target features, a classification result corresponding to the target object.

The foregoing image processing apparatus 1000 is configured to: obtain the at least two images formed by separately capturing the same target object from different imaging angles, separately extract, by using feature extraction networks corresponding to the images in an image processing model, target features of the images respectively corresponding to the feature extraction networks, and further determine, according to the target features, the classification result corresponding to the target object. On the one hand, a machine learning model automatically learns of the features in the image, and further obtains the classification result without manual participation, thereby improving processing efficiency and processing accuracy. On the other hand, the classification result is determined by combining the images formed by separately capturing the same target object from different imaging angles, thereby effectively improving classification accuracy.

In an embodiment, the classification result determining module 1006 may be configured to: perform classification according to the target features through the fully connected layer in the image processing model, to determine the classification result corresponding to the target object.

In an embodiment, the image processing apparatus 1000 further includes: an intermediate feature obtaining module, configured to sequentially perform convolution through a convolution layer in the image processing model and perform pooling through a pooling layer in the image processing model on the first target feature and the second target feature, to obtain intermediate features. Accordingly, the classification result determining module 1006 may be configured to: perform classification according to the intermediate features through the fully connected layer in the image processing model, to determine the classification result corresponding to the target object.

In an embodiment, the image processing apparatus 1000 may further include a model training module. The model training module may include the following units: a global sample obtaining unit, configured to obtain at least two global image sample groups, the global image sample groups being formed by separately capturing a sample object from different imaging angles; an intermediate network training unit, configured to: separately perform model training of a first neural network according to the global image sample groups, and determine intermediate feature extraction networks corresponding to the global image sample groups; a neural network construction unit, configured to construct a second neural network according to the intermediate feature extraction networks; and an image processing model training unit, configured to: perform model training of the second neural network according to the global image sample groups, and determine the image processing model.

In an embodiment, the model training module may further include the following units: a first initial parameter obtaining unit, configured to perform parameter initialization processing on a first initial neural network, to obtain first initial parameters; and a first network determining unit, configured to determine the first neural network according to the first initial parameters.

In an embodiment, the model training module may further include the following units: a local sample obtaining unit, configured to obtain a local image sample of a target region including a sample object; a second initial parameter obtaining unit, configured to perform parameter initialization processing on a second initial neural network, to obtain a second initial parameter; and a second network determining unit, configured to: perform model training of the second initial neural network according to the local image sample and the second initial parameter, and determine the first neural network.

In an embodiment, the local image sample includes a medical image sample, and the target region includes a lesion region.

In an embodiment, the image may include a medical image.

In an embodiment, the at least two images include: a mammary molybdenum target image formed by capturing a breast in a CC position and a mammary molybdenum target image formed by capturing the breast in an MLO position.

For other various features and aspects of the image processing apparatus, the above descriptions provided for the image processing method may be referred to. Details are not described herein again. The modules in the foregoing image processing apparatus may be implemented entirely or partially by software, hardware, or a combination thereof. The foregoing modules may be built in or independent of a processor of a computer device in a hardware form, or may be stored in a memory of the computer device in a software form, so that the processor invokes and performs an operation corresponding to each of the foregoing modules.

Figure 11:
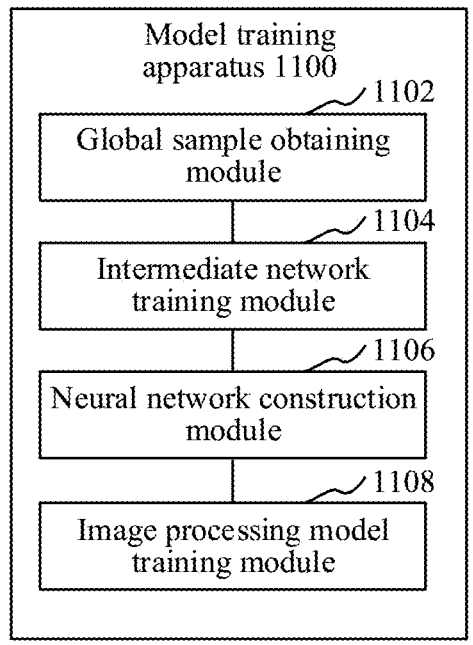
FIG. 11 is a structural block diagram of another model training apparatus according to an embodiment of the disclosure.

In some embodiments, as shown in FIG. 11, a model training apparatus 1100 is provided. The apparatus may be disposed in a computer device, and may include the following modules 1102 to 1108.

A global sample obtaining module 1102 is configured to obtain at least two global image sample groups, the global image sample groups being formed by separately capturing a sample object from different imaging angles.

An intermediate network training module 1104 is configured to: separately perform model training of a first neural network according to the global image sample groups, and determine intermediate feature extraction networks corresponding to the global image sample groups.

A neural network construction module 1106 is configured to construct a second neural network according to the intermediate feature extraction networks.

An image processing model training module 1108 is configured to: perform model training of the second neural network according to the global image sample groups, and determine an image processing model.

In an embodiment, the model training apparatus 1100 may further include the following modules: a first initial parameter obtaining module, configured to perform parameter initialization processing on a first initial neural network, to determine first initial parameters; and a first network determining module, configured to determine the first neural network according to the first initial parameters.

In an embodiment, the model training apparatus 1100 may further include the following modules: a local sample obtaining module, configured to obtain a local image sample of a target region including a sample object; a second initial parameter obtaining module, configured to perform parameter initialization processing on a second initial neural network, to determine a second initial parameter; and a second network determining module, configured to: perform model training of the second initial neural network according to the local image sample and the second initial parameter, and determine the first neural network.

In an embodiment, the local image sample includes a medical image sample, and the target region includes a lesion region.

For other features and aspects of the model training apparatus, the above descriptions provided for the model training method may be referred to. Details are not described herein again. The modules in the foregoing model training apparatus may be implemented entirely or partially by software, hardware, or a combination thereof. The foregoing modules may be built in or independent of a processor of a computer device in a hardware form, or may be stored in a memory of the computer device in a software form, so that the processor invokes and performs an operation corresponding to each of the foregoing modules.

In an embodiment, a computer device is provided, including a memory and a processor, the memory storing a computer program, the computer program, when executed by the processor, implementing the operations of the image processing method and/or the model training method provided in any embodiment of the disclosure.

In an embodiment, the computer device may be a terminal 110 in FIG. 1. An internal structure diagram of the computer device may be shown in FIG. 12. The computer device includes a processor, a memory, and a network interface, a display screen, and an input apparatus connected through a system bus. The processor is configured to provide computation and control abilities. The memory includes a non-volatile storage medium and an internal memory. The non-volatile storage medium stores an operating system and a computer program, and the internal memory provides an environment for running the operating system and the computer program in the non-volatile storage medium. The computer program is executed by the processor, to implement the image processing method and/or the model training method. The network interface is configured to connect to and communicate with an external terminal by using a network. The display screen may be a liquid crystal display screen or an electronic ink display screen. The input apparatus of the computer device may be a touch layer covering the display screen, or may be a button, a trackball, or a touch panel disposed on a housing of the computer device, or may be an external keyboard, a touch panel or a mouse.

In an embodiment, the computer device may be the server 120 shown in FIG. 1. An internal structure of the computer device may be shown in FIG. 13. The computer device includes a processor, a memory, a network interface, and a database connected by using a system bus. The processor is configured to provide computation and control abilities. The memory includes a non-volatile storage medium and an internal memory. The non-volatile storage medium stores an operating system, a computer program, and a database, and the internal memory provides an environment for running the operating system and the computer program in the non-volatile storage medium. The database is configured to store image samples. The network interface is configured to connect to and communicate with an external terminal by using a network. The computer program is executed by the processor to implement the image processing method and/or the model training method.

Figure 12:
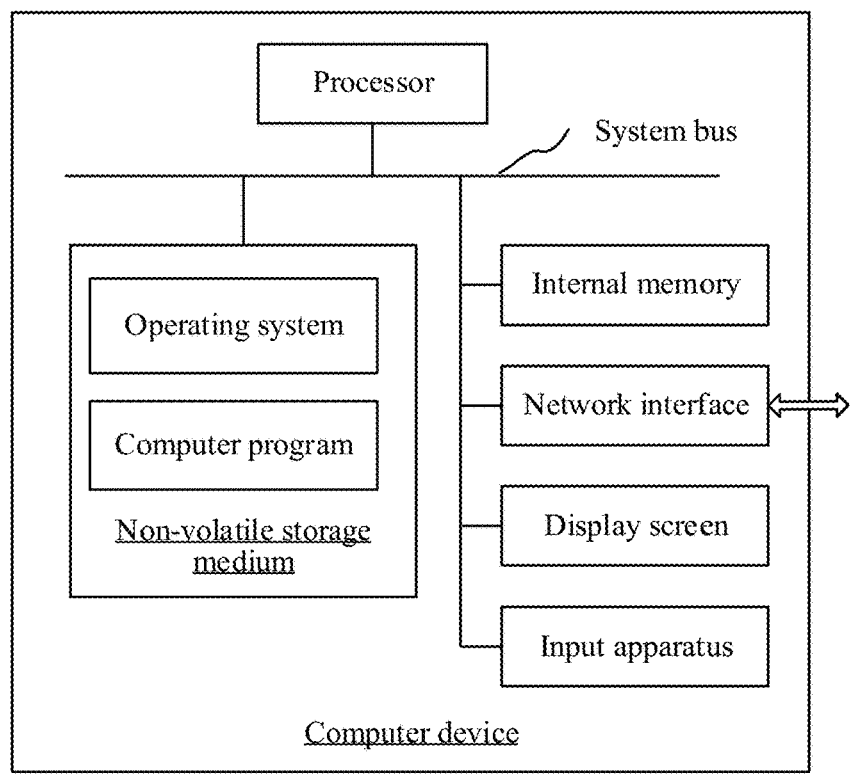
FIG. 12 is a structural block diagram of a computer device according to an embodiment of the disclosure.
Figure 13:
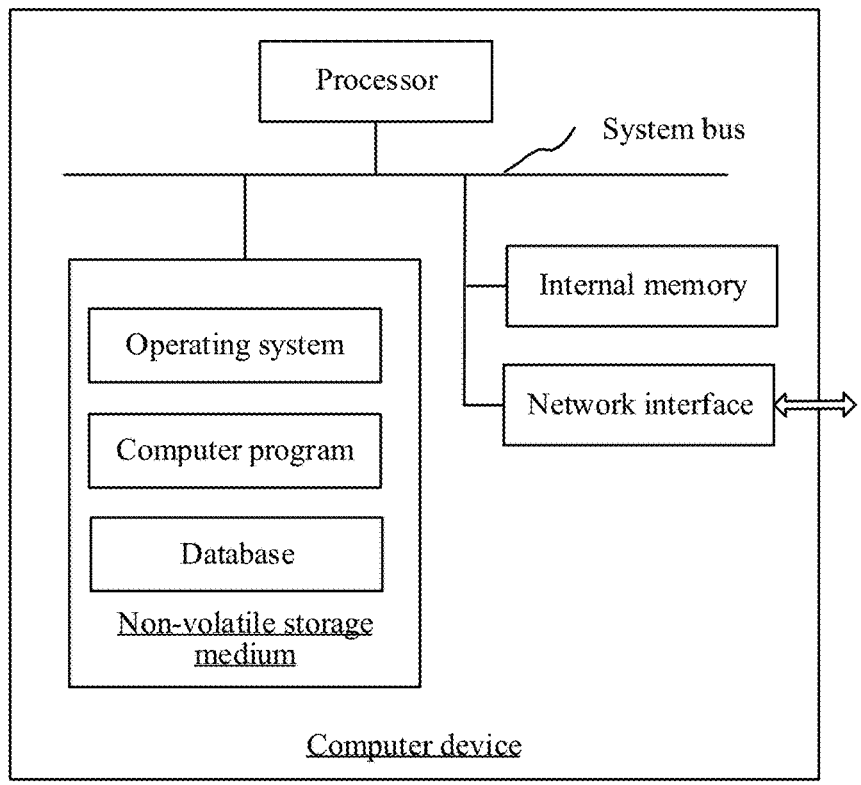
FIG. 13 is a structural block diagram of another computer device according to an embodiment of the disclosure.

A person skilled in the art may understand that the structure shown in FIG. 12 and FIG. 13 is only a block diagram of a partial structure related to the solution of the disclosure, and does not limit the computer device to which the solution of the disclosure is applied. Specifically, the computer device may include more or fewer components than those shown in the figure, or some components may be combined, or different component deployment may be used.

In an embodiment, the image processing apparatus provided in the disclosure may be implemented in a form of a computer program, and the computer program may be run on the computer device shown in FIG. 12 and FIG. 13. The memory of the computer device may store program modules forming the Image processing apparatus, for example, the Image obtaining module 1002, the target feature obtaining module 1004, and the classification result determining module 1006 shown in FIG. 10. The computer program formed by the program modules causes the processor to perform the operations in the image processing method in the embodiments of the disclosure described in this specification. For example, in the computer device shown in FIG. 12 and FIG. 13 may perform operation S202 by using the image obtaining module 1002, perform operation S204 by using the target feature obtaining module 1004, perform operation S206 by using the classification result determining module 1006, and the like, in the image processing apparatus shown in FIG. 10.

In an embodiment, the model training apparatus provided in the disclosure may be implemented in a form of a computer program, and the computer program may be run on the computer device shown in FIG. 12 or FIG. 13. The memory of the computer device may store program modules forming the model training apparatus, for example, the global sample obtaining module 1102, the intermediate network training module 1104, the neural network construction module 1106, and the image processing model training module 1108 shown in FIG. 11. The computer program formed by the program modules causes the processor to perform operations in the model training method in the embodiments of the disclosure described in this specification. For example, the computer device shown in FIG. 12 and FIG. 13 may perform operation S802 by using the global sample obtaining module 1102, perform operation S804 by using the intermediate network training module 1104, perform operation S806 by using the neural network construction module 1106, perform operation S808 by using the image processing model training module 1108, and the like, in the model training apparatus shown in FIG. 11.

A person of ordinary skill in the art may understand that all or some of procedures of the method in the foregoing embodiments may be implemented by a computer program instructing relevant hardware. The program may be stored in a non-volatile computer-readable storage medium. When the program is executed, the procedures of the foregoing method embodiments may be implemented. Any reference to a memory, a storage, a database, or another medium used in the embodiments provided in the disclosure can include a non-volatile and/or volatile memory. The non-volatile memory may include a read-only memory (ROM), a programmable ROM (PROM), an electrically programmable ROM (EPROM), an electrically erasable programmable ROM (EEPROM), a flash memory, or the like. The volatile memory may include a random access memory (RAM) or an external cache. As an illustration instead of a limitation, the RAM is available in various forms, such as a static RAM (SRAM), a dynamic RAM (DRAM), a synchronous DRAM (SDRAM), a double data rate SDRAM (DDRSDRAM), an enhanced SDRAM (ESDRAM), a synchronization link (Synchlink) DRAM (SLDRAM), a rambus direct RAM (RDRAM), a direct rambus dynamic RAM (DRDRAM), and a rambus dynamic RAM (RDRAM).

Therefore, in an embodiment, a computer-readable storage medium is provided, storing a computer program, the computer program, when executed by a processor, implementing the image processing method and/or the model training method provided in any embodiment of the disclosure.

The technical features in the foregoing embodiments may be randomly combined. For concise description, not all possible combinations of the technical features in the embodiment are described. However, provided that combinations of the technical features do not conflict with each other, the combinations of the technical features are considered as falling within the scope described in this specification.

According to the technical solutions provided in the embodiments of the disclosure, the at least two images formed by separately capturing the same target object from different imaging angles are obtained, target features of the images respectively corresponding to feature extraction networks are separately extracted through the feature extraction networks corresponding to the images in an image processing model, and the classification result corresponding to the target object is further determined according to the target features. A machine learning model automatically learns of the features in the image, and further obtains the classification result without manual participation, thereby improving processing efficiency and processing accuracy. The classification result is determined by combining the images formed by separately capturing the same target object from different imaging angles, thereby effectively improving classification accuracy.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

While the disclosure has been particularly shown and described with reference to example embodiments thereof, it will be understood that various changes in form and details may be made therein without departing from the spirit and scope of the following claims.

What is claimed is:

1. An image processing method, applied to a computer device, the method comprising:
    obtaining at least two images, the at least two images being based on the same target object captured from different imaging angles, respectively;
    obtaining an image processing model, and extracting, by using feature extraction networks included in the image processing model, target features of the at least two images, the feature extraction networks being configured to extract features of images corresponding to the different imaging angles, respectively; and
    determining, based on the target features, a classification result corresponding to the target object,
    wherein the obtaining the image processing model comprises:
    obtaining at least two global image sample groups, the at least two global image sample groups being based on a sample object captured from the different imaging angles;
    performing model training of a first neural network based on the at least two global image sample groups, and determining at least two intermediate feature extraction networks respectively corresponding to the at least two global image sample groups;
    constructing a second neural network using the at least two intermediate feature extraction networks; and
    performing model training of the second neural network that simultaneously receive two or more of the at least two global image sample groups, and obtaining the image processing model based on the trained second neural network.

2. The method according to claim 1, wherein the determining the classification result comprises:
    sequentially performing convolution through a convolution layer in the image processing model and performing pooling through a pooling layer in the image processing model on the target features, to obtain intermediate features; and
    determining the classification result corresponding to the target object based on the intermediate features through a fully connected layer in the image processing model.

3. The method according to claim 2, wherein the images comprise a medical image; and
    wherein the at least two images comprise a mammary molybdenum target image obtained by capturing a breast in a craniocaudal position and a mammary molybdenum target image obtained by capturing the breast in a mediolateral oblique position.

4. The method according to claim 1, wherein the obtaining the image processing model further comprises:
  performing parameter initialization processing on a first initial neural network, to obtain first initial parameters; and
  determining the first neural network based on the first initial parameters.

5. The method according to claim 1, wherein the obtaining the image processing model further comprises:
  obtaining a local image sample of a target region of the sample object;
  performing parameter initialization processing on a second initial neural network, to obtain a second initial parameter; and
  performing the model training of the second initial neural network based on the local image sample and the second initial parameter, to obtain the first neural network.

6. The method according to claim 5, wherein the local image sample comprises a medical image sample, and the target region comprises a lesion region.

7. A non-transitory computer-readable storage medium, storing a computer program, the computer program, when executed by a processor, causing the processor to perform operations of the method of claim 1.

8. A computer device, comprising a memory and a processor, the memory storing a computer program, when executed by the processor, causing the processor to perform operations of the method according to claim 1.

9. A model training method, applied to a computer device, the method comprising:
  obtaining at least two global image sample groups, the at least two global image sample groups being based on a sample object captured from different imaging angles, respectively;
  performing model training of a first neural network based on the at least two global image sample groups, and determining at least two intermediate feature extraction networks corresponding to the at least two global image sample groups;
  constructing a second neural network according to the at least two intermediate feature extraction networks; and
  performing model training of the second neural network based on the at least two global image sample groups, obtaining an image processing model based on the trained second neural network, the image processing model comprising feature extraction networks configured to extract features of images corresponding to the different imaging angles, respectively.

10. The method according to claim 9, further comprising determining the first neural network, wherein the determining the first neural network comprises:
  performing parameter initialization processing on a first initial neural network, to obtain a first initial parameter; and determining the first neural network based on first initial parameters; or
  obtaining a local image sample of a target region comprising the sample object; performing parameter initialization processing on a second initial neural network, to obtain a second initial parameter; and performing model training of the second initial neural network based on the local image sample and the second initial parameter, and determining the first neural network.

11. The method according to claim 10, wherein the local image sample comprises a medical image sample, and the target region comprises a lesion region.

12. A non-transitory computer-readable storage medium, storing a computer program, the computer program, when executed by a processor, causing the processor to perform operations of the method of claim 9.

13. A computer device, comprising a memory and a processor, the memory storing a computer program, when executed by the processor, causing the processor to perform operations of the method according to claim 9.

14. An image processing apparatus, disposed in a computer device, the apparatus comprising:
  at least one memory configured to store program code; and
  at least one processor configured to read the program code and operate as instructed by the program code, the program code comprising:
    image obtaining code configured to cause at least one of the at least one processor to obtain at least two images, the at least two images being based on the same target object captured from different imaging angles, respectively;
    target feature obtaining code configured to cause at least one of the at least one processor to extract, by using feature extraction networks in an image processing model, target features of the at least two images, the feature extraction networks being configured to extract features of images corresponding to the different imaging angles, respectively; and
    classification result determining code configured to cause at least one of the at least one processor to determine, based on the target features, a classification result corresponding to the target object,
  wherein the program code further comprises:
  obtaining code configured to cause at least one of the at least one processor to obtain at least two global image sample groups, the at least two global image sample groups being based on a sample object captured from the different imaging angles;
  first training code configured to cause at least one of the at least one processor to perform model training of a first neural network based on the at least two global image sample groups, and determine at least two intermediate feature extraction networks respectively corresponding to the at least two global image sample groups;
  constructing code configured to cause at least one of the at least one processor to construct a second neural network using the at least two intermediate feature extraction networks; and
  second training code configured to cause at least one of the at least one processor to perform model training of the second neural network that simultaneously receive two or more of the at least two global image sample groups, and obtain the image processing model based on the trained second neural network.

15. The apparatus according to claim 14, wherein the classification result determining code causes at least one of the at least one processor to:
  sequentially perform convolution through a convolution layer in the image processing model and performing pooling through a pooling layer in the image processing model on the target features, to obtain intermediate features; and
  determine the classification result corresponding to the target object based on the intermediate features through a fully connected layer in the image processing model.

16. The apparatus according to claim 14, wherein the first training code further causes at least one of the at least one processor to perform parameter initialization processing on a first initial neural network to obtain first initial parameters, and determine the first neural network based on the first initial parameters.

17. The apparatus according to claim 14, wherein the first training code further causes at least one of the at least one processor to obtain a local image sample of a target region of the sample object, perform parameter initialization processing on a second initial neural network to obtain a second initial parameter; and perform the model training of the second initial neural network based on the local image sample and the second initial parameter, to obtain the first neural network.

18. The apparatus according to claim 17, wherein the local image sample comprises a medical image sample, and the target region comprises a lesion region.

* * * * *